US012268909B2

(12) United States Patent
Tan

(10) Patent No.: US 12,268,909 B2
(45) Date of Patent: Apr. 8, 2025

(54) ELECTRICALLY HEATED RESPIRATOR

(71) Applicant: Weining Tan, Mississauga (CA)

(72) Inventor: Weining Tan, Mississauga (CA)

(*) Notice: Subject to any disclaimer, the term of this patent is extended or adjusted under 35 U.S.C. 154(b) by 108 days.

(21) Appl. No.: 17/919,263

(22) PCT Filed: Mar. 27, 2021

(86) PCT No.: PCT/CA2021/050402
§ 371 (c)(1),
(2) Date: Oct. 15, 2022

(87) PCT Pub. No.: WO2021/212208
PCT Pub. Date: Oct. 28, 2021

(65) Prior Publication Data
US 2023/0149747 A1    May 18, 2023

(51) Int. Cl.
*A62B 9/00* (2006.01)
*A61L 2/04* (2006.01)
*A62B 18/02* (2006.01)
*A62B 23/02* (2006.01)

(52) U.S. Cl.
CPC ............... *A62B 9/003* (2013.01); *A61L 2/04* (2013.01); *A62B 18/025* (2013.01); *A62B 23/025* (2013.01)

(58) Field of Classification Search
CPC ..... A62B 9/003; A62B 18/025; A62B 23/025; A61L 2/04
See application file for complete search history.

(56) References Cited

U.S. PATENT DOCUMENTS

| 4,793,343 A   | * | 12/1988 | Cummins, Jr. ........ A62B 18/08 |
|               |   |         |                          219/501 |
| 11,433,212 B1 | * | 9/2022  | Hafeman .......... A61M 15/0085  |
| 2016/0375276 A1 | * | 12/2016 | Martin .................... A62B 18/10 |
|               |   |         |                         128/207.12 |
| 2020/0003487 A1 | * | 1/2020  | Brown ...................... F25D 3/00 |
| 2020/0078210 A1 | * | 3/2020  | Yang ...................... A61F 7/007 |
| 2021/0353790 A1 | * | 11/2021 | Abbaszadegan .......... A61L 2/04 |
| 2023/0363473 A1 | * | 11/2023 | Topsakal ................ A41D 13/11 |

* cited by examiner

*Primary Examiner* — Steven O Douglas

(57) ABSTRACT

A set of designs for an electrically heated respirator/face mask to kill or deactivate airborne viruses and bacteria by creating a seamless thermal and/or humidity chamber/barrier around the wearer's nose and mouth area; in addition to efficiently filtering the tiny particles according to NIOSH N95 standards, it reduces the chance of contracting the disease. The designs include various combinations: a disposable or reusable N95 respirator with or without an exhalation valve, disposable or reusable medical face mask, both with or without integrated and replaceable filter layers, and a reusable respirator with filter cartridges. Each design comprises multiple layers with an active thermal filter with a heating element, which is made of graphene. The respirator is connected via a USB cable to a power unit. A control module is used to turn the device on and off and optionally control the inner temperature and humidity through sensors.

20 Claims, 7 Drawing Sheets

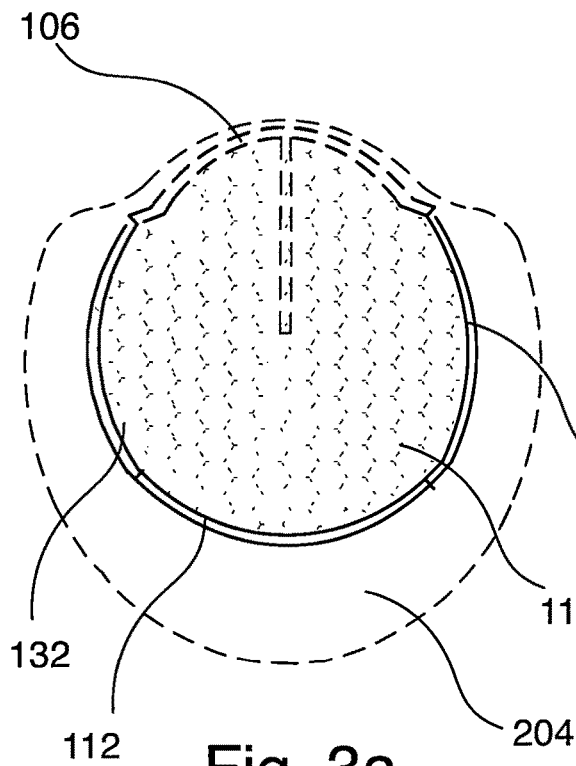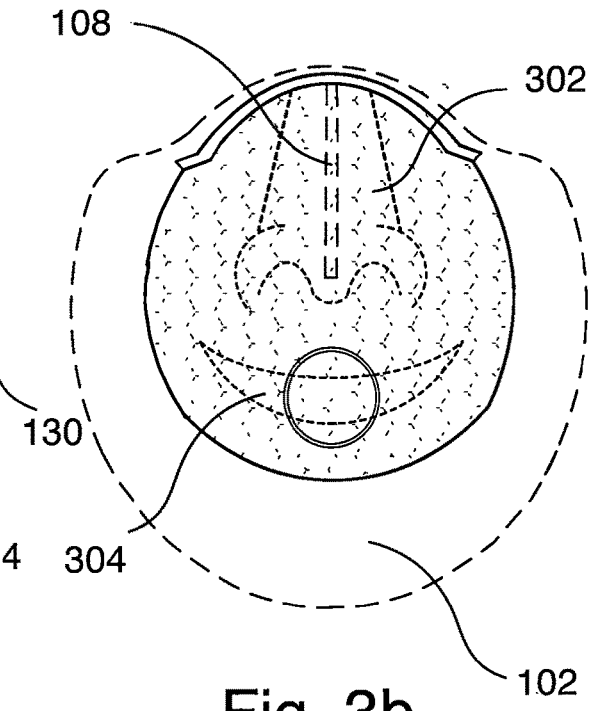
Fig. 3a    Fig. 3b
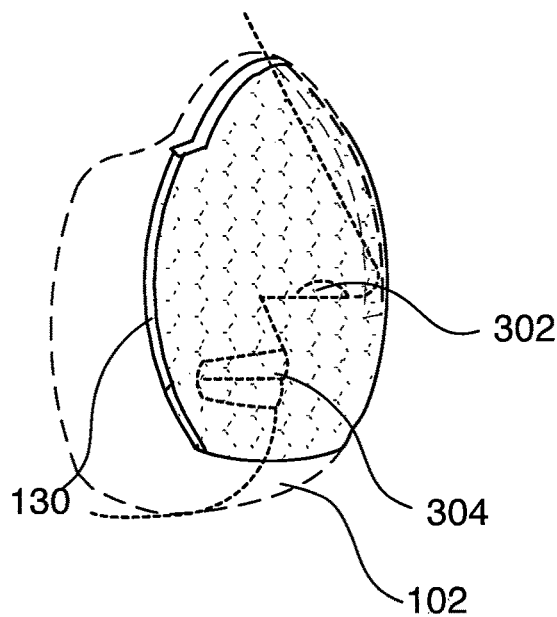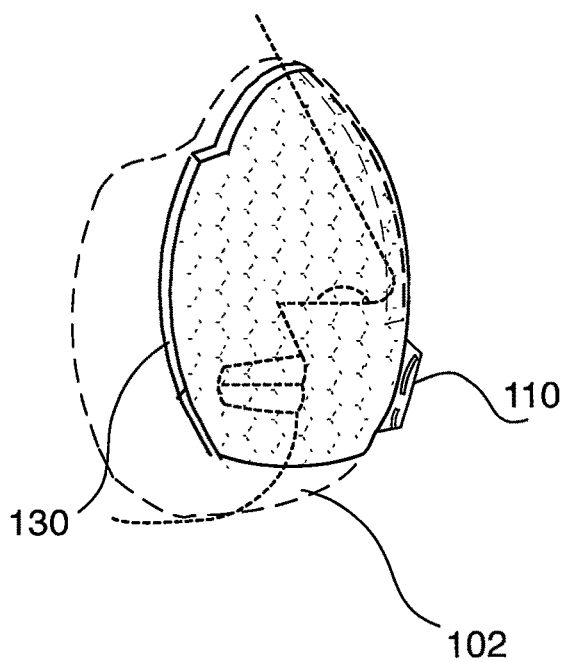
Fig. 3c

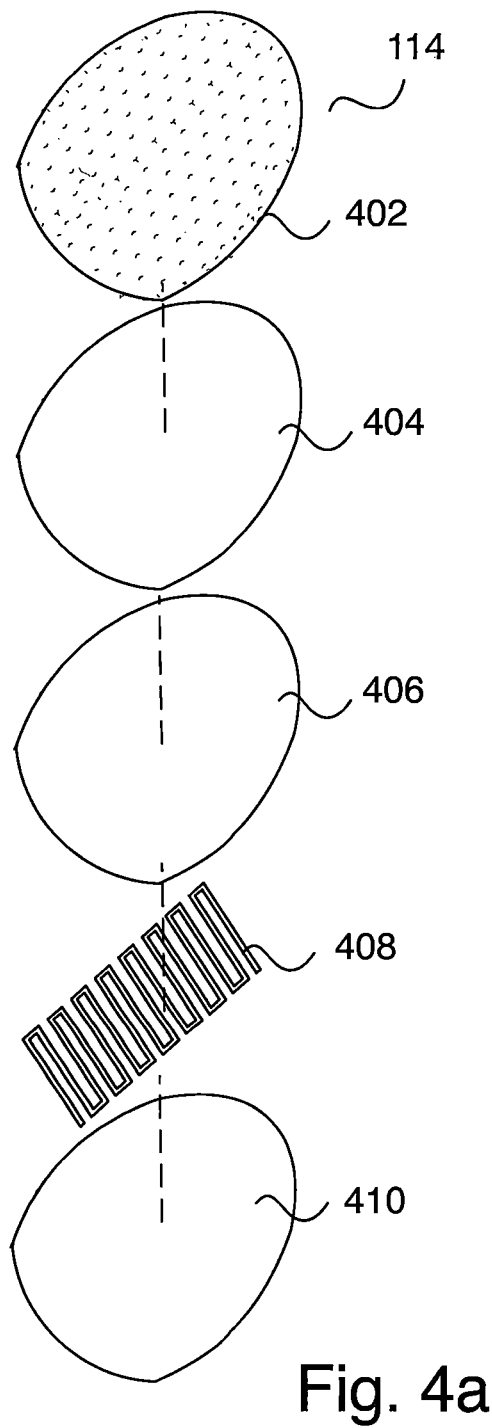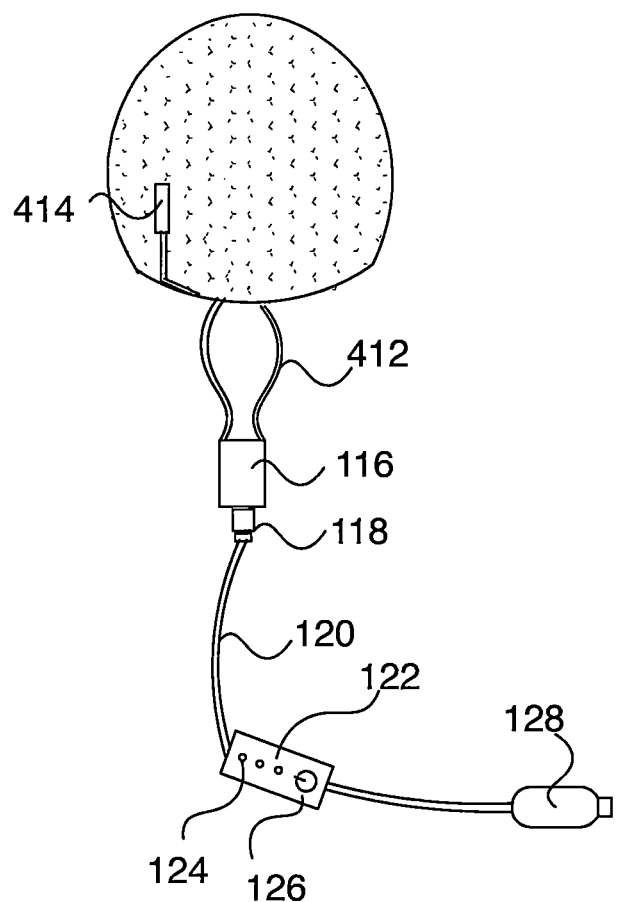
Fig. 4a
Fig. 4b

ELECTRICALLY HEATED RESPIRATOR

CROSS-REFERENCE TO RELATED APPLICATIONS

This application is a national stage application, filed under 35U.S.C. § 371 of International Patent Application No. PCT/US2021/050402, the priority date is Apr. 22, 2020, and filed on Mar. 27, 2021, which is incorporated by reference herein in its entirety.

FIELD

The present disclosure is in the field of public health and medical devices, bacterial or viral diseases, COVID-19 and other coronaviruses, respirator, face mask, meltblown filter, electrical heating, graphene, temperature regulation, and especially, an electrically heated high-efficiency respirator with a thermal barrier around the nose and mouth for antiviral and medical protection.

BACKGROUND

Infections or diseases are caused by tiny organisms or pathogens, primarily bacteria and viruses. The terms 'bacteria' and 'viruses' can be considered interchangeable with 'pathogens.' The spread of bacteria and viruses are most commonly transmitted through respiratory droplets in the air via coughing or sneezing, contact with bodily fluids, or contact with an infected surface. Without proper protective measures, diseases caused by bacteria or viruses can quickly spread from person to person; this leads to epidemics or pandemics such as SARS or the recent novel coronavirus known as COVID-19.

Medical devices are actively developed to protect people and prevent the spread of infections and diseases—particularly airborne diseases. Among them; face masks and respirators are among the most commonly used devices to protect the wearer from spreading and inhaling hazardous atmospheres, including fumes, vapors, gases, and particulate matter such as dust and airborne microorganisms.

A face mask is a loose-fitting mask that covers the nose and mouth area. They have two ear loops that stretch around the ears to hold the mask in place. Face masks are designed to be used as one-way protection only, capturing large particles or droplets from the wearer and preventing them from being spread to the environment. In contrast, a respirator is a tight-fitting mask that creates a facial seal. When used properly, it will create a facial seal that provides two-way protection, filtering the air entering and exiting the wearer at a level of efficiency designated by the respirator or filter/cartridge (half-face and full-face). Respirators come in three distinct categories: Disposable, Half-face, and Full-face. In the present disclosure, we ignore the major differences between face masks and respirators, consider a face mask is a special type of half-faced respirators. Both face masks and respirators can be disposable and reusable. Hereinafter, we refer to face mask and respirator interchangeably.

Respirators range from relatively inexpensive, single-use, disposable models to more robust and reusable models with replaceable cartridges, often called reusable or non-disposable respirators. All can be used to prevent a contagious patient from spreading the virus to other healthy people or protect a healthy person from getting infected from an ill person or other virus sources.

Disposable respirators primarily come in the following two varieties: a surgical face mask and an N95 respirator. Both masks catch liquid droplets that may contain bacteria or viruses. The surgical face mask, also interchangeably referred to as a face mask or surgical mask, is a loose-fitting, flat, flexible, pleated, or duck-billed shaped, disposable device with multiple layers of filters. The surgical mask is fastened to the head with ear loops; it creates a physical barrier between the mouth and nose of the wearer and potential contaminants in the immediate environment. Face masks are cheaper, easier to use, and are loose-fitting for better breathability. However, they are designed to be disposed of after a single-use, although this also means little to no maintenance. During use, the effectiveness gradually decreases before replacement is required. Furthermore, the edges of the mask do not form a reliable seal around the nose and mouth, meaning that the bacteria or virus can still enter the mask opening. A face mask might be useful in reducing the spread of airborne pathogens; however, its function in this regard is limited.

The N95 respirator is another disposable respirator designed to achieve a more efficient filtration of airborne particles and a very close facial fit. Being NIOSH-approved, the N95 is considered adequate for protection against PM2.5, which refers to atmospheric particulate matter (PM) with a diameter smaller than 2.5 micrometers, as well as most viruses and bacteria. Also, the edges of the respirator are designed to form a seal around the nose and mouth. Surgical N95 Respirators are commonly used in the health care environment and are a subset of N95 Filtering Facepiece Respirators (FFRs), often referred to as N95s. In the wake of the COVID-19 pandemic, this particular respirator has increased in popularity. It is considered a NIOSH-approved device along with other associated devices, including the N/R/P-95/99/100 series respirators.

More advanced respirators can protect users, usually professionals, better. In addition to having multiple layers for catching airborne substances, such devices may have additional mechanisms such as filter cartridges to hold replaceable filters in between. They can also come with or without an exhalation valve. The edges of the device form a tight-fitting seal around the nose and mouth. Such respirators may be made of different materials (e.g., plastic, rubber, or metal), and therefore, are reusable with regular cleaning and maintenance. On the other hand, these respirators have higher breathing resistance and can be hard to wear for long periods of time. The device can also be more expensive, less comfortable due to its size and weight, and needs periodic maintenance (e.g., regularly replacing cartridges and filters).

Some respirators include an exhalation valve, which opens to release exhaled air and closes during inhalation so that fresh air comes through the filter. This helps to reduce excessive dampness (moisture) and heat during exhalation. A healthy person may prefer to use a respirator with an exhalation valve; however, it should not be worn by a patient because their breath may contain infectious particles and droplets. Health care workers may wear respirators with exhalation valves unless the patient has a medical condition (such as an open wound), for which a health care worker would typically wear a surgical face mask to protect the patient.

One general problem with such devices is that any openings allow bacterial or viral pathogens to enter through and infect the wearer. Factors include, but are not limited to: the edges are not sealed tightly enough; the filter levels are not correct; the number of filter layers is insufficient; the filters are worn down or expired. Thus, the device cannot ensure reliable protection against germs, viruses, especially highly contagious viruses like COVID-19, SARS, etc. Other problems include higher supply costs, difficulty in obtaining, regular replacement of cartridges if applicable, and more waste created from disposable devices.

For ideal protection, filtering and capturing viruses and bacteria are not always enough; it would be better to kill or deactivate the pathogens if it is possible. This can be commonly done with chemicals, humidity, or heat. Chemical treatment is more common but can be hazardous or have side-effects if not handled properly. Other existing medical devices have been developed with antimicrobial properties in their materials. Humidity or heat is typically a relatively safer choice, and most viruses and bacteria cannot survive high temperatures and humidity. Pathogens from most infections/diseases, including COVID-19, are killed or deactivated proportional to the temperature and humidity in their environment or when it reaches a certain threshold. Some heated or moisturizing devices have been previously developed for medical use; however, none have developed a respirator with a heating mechanism for killing or deactivating viruses and/or bacteria.

Existing heated face masks and respirators have been developed primarily for warmer breathing in extremely low-temperature environments. However, they are not designed for medical use yet. Their protection against viral diseases, for example, is limited since their temperature (20-40° C.) is not high enough to deactivate any bacteria or virus. There is a need to incorporate a mechanism in a respirator to generate an environment around the human nose and mouth that kills or deactivates a virus whenever it enters or exits the human's respiratory system through the respirator.

Existing heated devices also have bulky electrical components that take up a lot of space. Other challenges for heated respirators include a need to be able to set the temperature, keep the temperature constant, and lower power usage to control the device effectively.

The present disclosure provides designs for a new respirator device with increased protection by heating the nose and mouth areas to a higher temperature and/or controlling humidity or other environmental parameters to a predefined condition(s). The designs address the problem with exposure to viral/bacterial pathogens by creating a concealed invisible physical barrier, hereafter called the thermal filter, heat barrier, thermal barrier, or humidity barrier, interchangeably. The heat and/or humidity produced inside the respirator device is high enough to kill or deactivate viruses or bacteria from entering, exiting, and infecting the wearer and others in their proximity.

SUMMARY

The present disclosure provides new designs for an electrically controlled respiratory device with increased protection against viral and bacterial airborne diseases. The designs achieve the goal by introducing additional mechanisms of killing or deactivating viruses and bacteria along with the regular high-efficiency particle and droplet filtration of the respirator. The designs novelly create and maintain a local heat and/or humidity barrier in a confined space around the wearer's nose and mouth. The heat and humidity form a seamless seal around the wearer's face, which helps kill and deactivate various pathogens in the inhaled and exhaled air. Therefore, the heat and humidity further protect the wearer from spreading the virus out into or getting infected from the environment.

The designs include various combinations related to the disposability, shape form factors, and filter types of the respirator. The present disclosure describes three exemplary embodiments: a disposable or reusable N95 respirator with or without an exhalation valve, disposable or reusable medical face mask with or without integrated and replaceable filter layers, and a reusable respirator with filter cartridges. Each design is comprised of multiple layers with an active thermal filter with or without a passive particle filter, such as the NIOSH N95 filter. The thermal filter contains a heating element made of graphene. The graphene is strong, flexible, and has superior thermal conductivity. The respirator also comprises a chamber around the nose and mouth; the thermal filter is located in this chamber and is heated to a temperature high enough to kill or deactivate viruses or bacteria. A thermostat and/or a humidity sensor inside the chamber can be used to control the temperature and humidity. The temperature can be controlled by starting and stopping the heating element according to the thermostat measurement. The humidity can also be controlled according to sensor feedback. This adjustment can be made with the installation of the optional exhalation valve and/or a small electrical fan in it. The opening of the exhalation valve can be adjusted manually or electrically. Also, if installed, the fan's speed can be controlled electrically. The respirator is connected electrically via a USB connection. When connected, a power switch/control module can be used to turn the device on and off and adjust the heating or humidity levels of the device with multiple presets. The power is sent to the heating element through the USB cable, which then heats the device. A built-in microprocessor controls everything in the device, including the presets, heating, humidity adjustment, and operation timing, etc.

BRIEF DESCRIPTION OF THE DRAWINGS

FIG. 3a illustrates a rear view of an N95 disposable or reusable respirator applied on a person's face in the preferred embodiment of the present disclosure.

FIG. 3b illustrates a front view of an N95 disposable or reusable respirator applied on a person's face in the preferred embodiment of the present disclosure.

FIG. 3c illustrates a side view of an N95 disposable or reusable respirator applied on a person's face in the preferred embodiment of the present disclosure.

FIG. 4a illustrates an exploded isometric view of the multiple layers of the heating element in the preferred embodiment of the present disclosure.

FIG. 4b illustrates the heating element's connection to the power switch and temperature controller chip in the preferred embodiment of the present disclosure.

DETAILED DESCRIPTION

Figure 1:
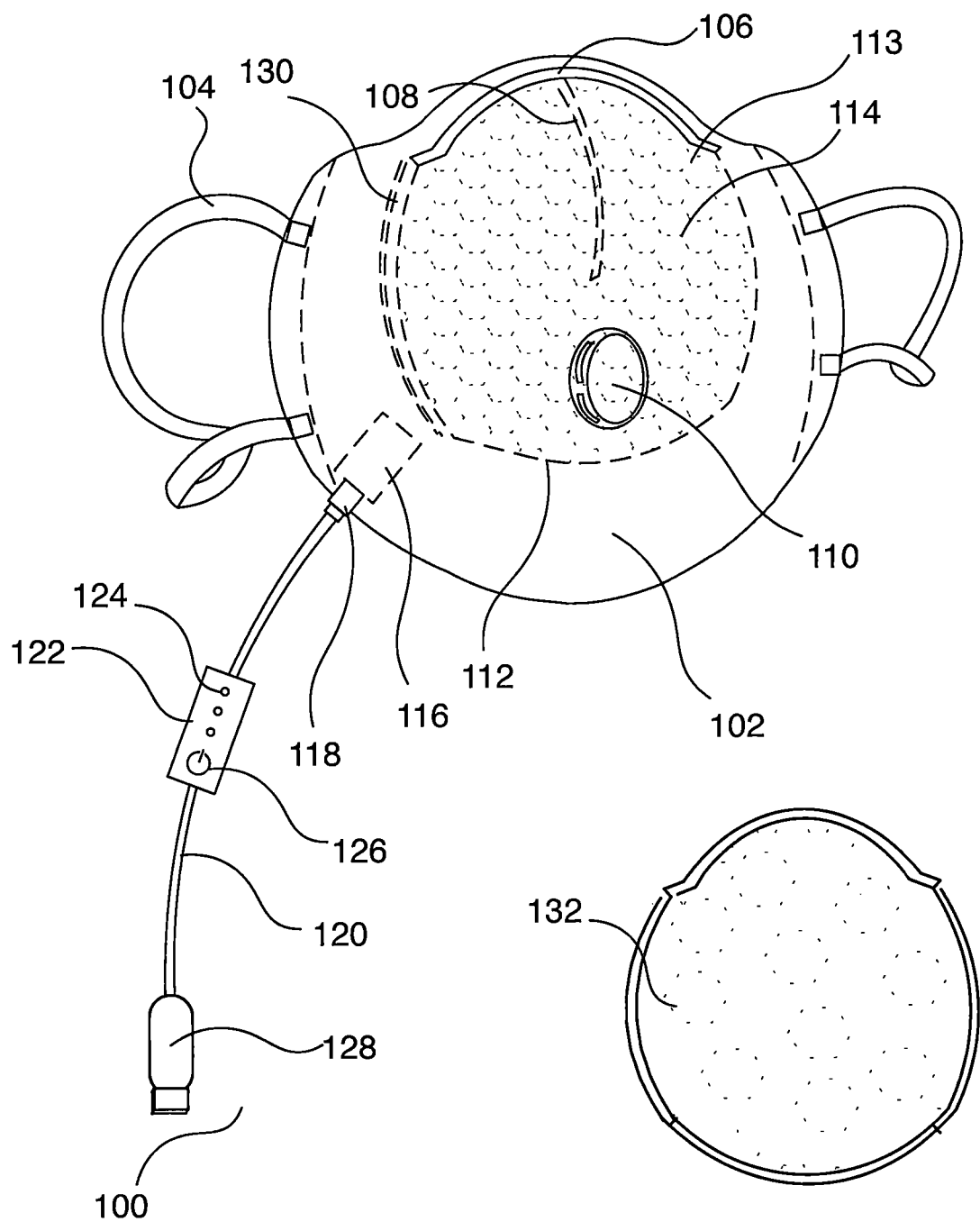
FIG. 1 illustrates an isometric view of an electrically heated N95 disposable or reusable respirator and a front view of the replaceable filter in the preferred embodiment of the present disclosure.

The language employed herein only describes particular embodiments; however, it is not intended to be limited to the specific embodiments of the disclosure. Within the disclosure, the term "and/or" includes any and all combinations of one or more associated items. Unless indicated, "a", "an", and "the" can encompass both the singular and plural forms within the disclosure. It should also be noted that "they", "he/she", or "he or she" are used interchangeably because "they", "them", or "their" are now considered singular gender-neutral pronouns. The terms "comprises" and/or "comprising" in this specification should specify the presence of stated features, steps, operations, elements, and/or components; however, they do not exclude the presence or addition of other features, steps, operations, elements, components, and/or groups. Unless otherwise defined, all terminology used herein, including technical and scientific terms, have the same definition as what is commonly understood by one ordinarily skilled in the art, typically to whom this disclosure belongs. It will be further understood that terms, such as those defined in commonly used dictionaries, should be interpreted as having the same meaning as defined in the context of the relevant art and the present disclosure; such terms will not be construed in a romanticized or overly strict sense unless explicitly described herein. It should be understood that multiple techniques and steps are disclosed in the description, each with its own individual benefit. Each technique or step can also be utilized in conjunction with a single, multiple, or all of the other disclosed techniques or steps. For clarity, the description will avoid repeating each possible combination of the steps unnecessarily. Nonetheless, it should be understood that such combinations are within the scope of the disclosure and the claims.

In the following description, specific details are mentioned to give a complete understanding of the present disclosure. However, it may likely be evident to one ordinarily skilled in the art; hence, the present disclosure may be applied without the mention of these specific details. The present disclosure is represented as one realization; however, the disclosure is not necessarily limited to the specific embodiments illustrated by the figures or description below. The description of the present disclosure will now be interpreted by specifying the appended figures representing preferred or alternative embodiments.

The present disclosure provides novel designs for a respirator with an active electrically controlled thermal chamber, optional standardized passive particle filter, and exhalation valve. The new designs provide increased protection against viral and bacterial airborne diseases. The designs achieve the goal by introducing additional mechanisms of killing or deactivating viruses and bacteria along with the regular high-efficiency particle and droplet filtration of the respirator. The designs novelly create and maintain a local heat and/or humidity barrier in a confined space around the wearer's nose and mouth. The heat and humidity form a seamless seal around the wearer's face and help to kill and deactivate various pathogens in the inhaled and exhaled air; therefore, the heat and humidity further protect the wearer from spreading the virus out into or getting infected from the environment.

The designs include all combinations related to the disposability, shape form factors, and filter types of the respirator. For example, the respirator can be disposable or reusable; flat face mask or 3D-shaped N95 respirator; with an embedded particle filter layer or replaceable particle filter layer; medical use or nonmedical use, etc. The present disclosure describes the first three exemplary embodiments: a respirator with without an exhalation valve, a medical face mask with or without integrated and replaceable filter layers, and a reusable respirator with filter cartridges. The remaining combination embodiments are all deemed obvious to the ordinarily skilled in the art.

Each design is comprised of multiple layers with an active thermal filter with or without a passive particle filter, such as the NIOSH N95 passive particle filter. The heating element may be made of graphene. It is an ideal heating material that is strong, flexible, and has superior thermal conductivity and heating efficiency. The respirator also comprises a chamber around the nose and mouth; the thermal filter is located in this chamber and is heated to a temperature high enough to kill or deactivate viruses or bacteria through a heating element.

A thermostat and/or a humidity sensor located inside the chamber can be used to control the temperature and humidity. The temperature can be controlled by starting and stopping the heating element according to the thermostat measurement. The humidity can also be controlled according to sensor feedback. This adjustment can be made with the installation of the optional exhalation valve and/or a small electrical fan in it. The opening of the exhalation valve can be adjusted manually or electrically. Also, if installed, the fan's speed can be controlled electrically. The respirator is connected electrically via a USB connection. When connected, a power switch/control unit can be used to turn the device on and off and adjust the heating or humidity levels of the device with multiple presets. The power is sent to the heating element through the USB cable, which then heats the device; a built-in micro-processing chip controls everything in the device, including the presets, heating, humidity adjustment, operation timing, etc.

For convenience, the terms 'respirator' and 'face mask' are considered interchangeable with 'device' hereinafter in the present disclosure. In a preferred embodiment, the respirator takes the shape and form factor of a typical NIOSH N-95 disposable or reusable respirator and operates similarly to one. The device is made up of multiple nonwoven layers, which may or may not have a particle filter layer and a shape supporting layer. The filter in the particle filter layer is replaceable. The device forms a seal around the user's face to prevent pathogens from entering to infect users or leaking out to infect other people. Additionally, there is a thermal filter with a heating and humidity mechanism around the nose and mouth area, where a chamber is created, kills, or deactivates pathogens that attempt to enter or exit. Unlike previously heated masks, the thermal chamber of the present disclosure can reach a high temperature ranging from 55° C. to 100° C., which is enough to kill pathogens without causing harm to the user's face. The heat kills pathogens entering the nostrils or mouth as the user actively breathes. Even at the device's-lower temperature setting above room temperature, it can still inhibit the activity of pathogens to reduce the risk of infection. This barrier is formed from the chamber inside the mask, whose size and shape can be adjusted by two perpendicular nose clips. This keeps the barrier focused on prominent openings for pathogens to enter or exit—the nostrils and mouth. There is also an optional exhalation valve, which expels moisture and heat from exhalation while filtering air from inhalation. This valve allows increased comfort for prolonged use. The valve operation can be controlled by a central controlling circuit and a humidity sensor inside the chamber. The controlling of the exhalation valve can adjust the humidity inside the chamber, which can be raised to humidity levels high enough to kill or deactivate viruses and bacteria.

The disposable or reusable N95 respirator, especially the medical N95 respirator that is FDA approved, is generally worn by medical and industrial professionals. If the exhalation valve option is not used, however, it can also be worn by the general public during a pandemic. If the exhalation valve option is used, anyone can wear it provided that they are not ill.

The NIOSH air filtration rating is the U.S. National Institute for Occupational Safety and Health (NIOSH)'s classification of filtering respirators. The ratings describe the device's ability to protect the wearer from dust and liquid droplets in the air. Air-purifying respirators (APR) have incorporated particulate filter elements. NIOSH Particulate Respirator Class Minimum Efficiency Levels include N95, R95, P95 (95%), N99, R99, P99 (99%); N100, R100, P100 (99.97%). Since filters are tested against the most penetrating particle size of 0.3 μm, an APR with a P100 classification would be at least 99.97% efficient at removing particles of this size. Particles with a size lower and greater than 0.3 μm are filtered at an efficiency greater than 99.97%. Although it is counterintuitive that particle sizes of less than 0.3 μm are filtered with greater efficiency, the forces which have the greatest impact on the effectiveness of filtration. (aerosol impaction, interception, and diffusion) are weakest at this size for filters tested by NIOSH. Any particle size of 2.5 μm is called PM2.5. So, the N95 has more effectiveness than a PM2.5 filter.

The novel design in the present disclosure can be designed with other embodiments in mind. One exemplary embodiment is the disposable or reusable medical face mask. The face mask has multiple layers like its counterpart and works in the same way. However, there are several key differences from the N95 disposable or reusable respirator: (1) the filter layer, if present, is integrated into the device and not replaceable; (2) it has no exhalation valve to prevent liquid respiratory droplets from escaping the valve; (3) it is flat, flexible and does not have a supporting layer; (4) its edges cannot form a tight seal around the nose and mouth, which mean that pathogens can still enter from the sides, though a metal horizontal nose clip can adjust the top edge of the face mask to better adapt along the face and nose. However, the built-in thermal filter will still be able to kill pathogens that sneaked in and prevent the user from becoming ill; (5) the chamber is adjustable with the horizontal nose clip integrated into the device. The face mask embodiment can be used by both health professionals and the general public. The face mask is ideal for those who are ill since the mask prevents liquid droplets (via respiration) from contaminating the surrounding environment.

The other exemplary embodiment is a reusable respirator, which also functions similarly to the disposable or reusable N95 respirator. However, there are other key differences: (1) the outer and inner layer materials are made of a completely different material (e.g., rubber, plastic, or metal), which can be washed; (2) the filter layer of other embodiments is allocated to filter cartridges between the exhalation valve and thermal layer. When the filters are worn out or expired, the cartridges can be easily replaced without unnecessary tampering. This type of respirator would be ideally used by those in professional industries-those in the medical profession or in industries where airborne particles are an issue. While the general public can also wear this embodiment, it is not as ideal due to the cost and lack of portability.

One heating product recently used in other health products, for example, massaging eye masks, is graphene-based. Graphene is an allotrope of carbon formed in a two-dimensional lattice upon a single layer of atoms. Apart from carbon, silver particles may be present to reduce the sheet resistance to 158.7 Ωsq-1. It is a strong, lightweight, and flexible material with superior thermal conductivity, which makes it flexible for portability. It is also considered a zero-gap semiconductor, which aids in electrical conductivity and operational efficiency (low voltage and immediate response). It can be also be heated at high temperatures within a quick time, making it superior to other existing heaters. This makes the graphene-based heater a promising potential candidate for various wearable heating applications. Now is the time to apply heating properties to the respirator for medical use.

A chip or circuitry may also be used to actively regulate temperature and/or humidity to maintain a preset value. A thermostat and/or humidity sensor may also be used to detect the temperature and humidity inside the respirator chamber. The existing solutions do not work for the present disclosure because the devices do not have the means to control humidity, and the temperature can never reach a sufficient level before causing adverse damage to the device or body. A new temperature regulation function and design of the present disclosure is required for medical face masks and respirators due to the increased temperature and additional humidity monitoring required to kill viral and/or bacterial pathogens.

The current research tells us that during a pandemic with an airborne disease, caused by a type of virus like COVID-19 coronavirus, the confirmed number of the infected cases rose in line with average temperatures up to a peak of 8.72° C., and then declined with warming temperatures as the stability of the 295 virus also decreased. During the 2003 SARS outbreak, for every rise in temperature by 1° C. in Hong Kong, the number of confirmed cases declined by 3.6. If the weather helps us reduce the transmissibility and environmental stability of the virus, then perhaps the chain of transmission can be broken.

One research study revealed that in higher temperatures, the temperature only affects only the virus' survival time and not its ability to infect. Similar results were found with the SARS coronavirus. SARS remains stable at 4° C. but will lose its activeness in three days at 37° C. and can survive for only 15 minutes at 70° C. A generally accepted conclusion from these studies is that the COVID-19 virus is sensitive to heat. The coronavirus effectively inactivates when exposed to a temperature of 56° C. (132.8° F.) for 30 minutes, or a higher temperature under less time. However, some research also showed that the viruses were heated to 60° C. (140° F.) for one hour and were still able to replicate. Generally, a temperature of 92° C. (197° F.) for 15 minutes was more effective than 56° C. (132.8° F.) for 30 minutes to achieve 6-log reduction.

Regarding the research on the survival times (in hours & days) of the coronavirus at relative humidity & air temperatures, we knew that the survival times at 40° C. (104° F.) for all of the following: at 20% RH (humidity) were more than 120 hours for proxies of coronaviruses on stainless steel; at 50% RH were more than 24 hours; at 80% RH became less than 7 hours. In this case, a combined high temperature and humidity of 70° C. (68° F.) and 80% RH might significantly reduce the virus' survival time to less than a few seconds.

So, in one of the preferred embodiments of the present disclosure, the humidity inside the chamber is set to be kept at 80% RH; while the temperature is set to four presets—37° C. (98.6° F.), 56° C. (132.8° F.], 70° C. (68° F.), and 92° C. (197° F.). Any combination of temperature and humidity settings can be included in the other embodiments of the present disclosure. A balanced consideration between choosing a higher temperature and humidity is always required.

All embodiments have a chamber heated by a heating element made of graphene. Other heaters and heating materials can also be used. As noted before, graphene is strong, flexible, and has superior thermal conductivity. Furthermore, it heats up to high temperatures within a short period of time (approximately five seconds). Its properties allow uniform temperature distribution throughout the product regardless of shape (e.g., flat or curved). In yet another alternative embodiment, the temperature preference can be set to three preset settings with a power switch that switches with each click of the ON/OFF button. All temperature settings are capable of inhibiting pathogens with the lowest set at room temperature (28° C.), the medium set at the minimum 55° C. for killing pathogens, and the maximum at a temperature of 65° C. It is possible for the device to reach a temperature of up to 100° C.

Electrical power for heating is supplied via a USB cable connection to the sockets of each embodiment. A low voltage (5V) is used to power the device. Due to the low power consumption, the device can last for hours or perhaps a whole day. The power switch connected to the USB cable is considered interchangeable between embodiments. By using a USB cable, the user can power the device with the use of a USB-powered device such as a laptop. Additionally, attaching the device to a USB-powered power bank allows portability for the device to be worn anywhere. The power switch has a simple ON/OFF button that powers the device on and off. As noted before, the button can be pressed to change temperature settings that the users can select by pressing the ON/OFF button during operation.

Additionally, thermal regulation is present to ensure that the mask stays at a constant temperature according to the user's preference. This steady-state temperature is maintained with a temperature controller chip connected to the power switch via a signal sent through a conducting wire. This ability to keep a constant temperature follows a process in the device, which powers the heating element on and off depending on the temperature reading of the sensor in the temperature controller chip. The power operation of the device is set under a time-dependent profile as an additional means of temperature regulation, safety, and programmable operation. Therefore, the device will power off after a programmable period of time.

Additionally, the design can be made for other applications. This includes allowing the user to breathe warm air in environments with extremely cold temperatures, enabling the facial treatment, massaging, keeping moisture around the face where the thermal filter is located, etc.

FIG. 1 illustrates an isometric view of an electrically heated N95 disposable or reusable respirator and a front view of the replaceable filter in the preferred embodiment of the present disclosure. The front of the respirator (100) has an outer protective layer (113) with edges that form a seal around the face, particularly around the nose, mouth, and chin areas. The two sides of the respirator have elastic straps (104) that are placed around the user's ears. There is a thin horizontal metal nose clip (106) placed along the top edge of the respirator (100). This clip (106) is bendable around the bridge of the nose by manually pinching the clip (106). The respirator (100) also has a secondary nose clip, hereafter called the interior vertical nose clip (108), which is located in the respirator's (100) interior and bends along the user's nose vertically. The two nose clips (106, 108) are adjustable for better custom fitting around the user's face. The combined effect of adjusting the horizontal and vertical nose clips (106, 108) can form a small chamber (112) between the respirator (100) and the human face around the nose and mouth area. An exhalation valve (110) is located below the nose clips (106, 108), which line up with the mouth for inhalation/exhalation. Inside the chamber area (112), there is an embedded heating element (114) made of graphene or other heating materials. The two nose clips (106, 108), exhalation valve (110), and heating element (114) are essential in the function of the thermal filter around the nose and mouth; this will be explained in future paragraphs and in FIG. 3. The device (100) has a clipping mechanism (130) to install and replace the replaceable passive particle filter piece (132). In one embodiment of the present disclosure, the replaceable filter piece (132) is integrated with the inner layer (102), and these layers are replaced simultaneously; this will be noted in future paragraphs and in FIG. 2. The front view of the filter shows that the shape matches that of the chamber (112) and the heating element (114). The filter piece (132) is located between the inner layer (102) and heating element (114) and may have a single or multiple meltblown nonwoven layers; this will be explained later in future paragraphs and in FIG. 2.

The heating element (114) is powered electrically through a socket (116) that connects to a USB cable (120) via the USB socket connector (118). A power switch (122) controls the operation of the heating element (114) with the pressing of the ON/OFF button (126). Apart from turning on the device (100), the ON/OFF button (126) can also be pressed to adjust the heating level shown through three LED lights (124). The cable (120) has a USB power supply connector (128) that can connect to a device with a USB socket, such as a laptop, power bank, or outlet plug.

The chamber (112) with the heating element (114) and environmental sensors addresses the previous problem of existing respirators. Although most respirators (i.e., N95 and reusable) have a tight-fitting physical seal around the edge, it is not guaranteed that pathogens are entirely blocked at the physical seal. If the respirator is improperly fitted and/or needs fitting adjustments during its use, this may lead to additional contact with the device (100), which allows pathogens to enter and infect the user. Additionally, physical contact from contaminated hands is a way for pathogens to permeate the device (100). Heat around the chamber (112) can inhibit and kill pathogens before it can infect the user. The temperature settings are adjustable through the power switch (122); this and the sensors will be explained in future paragraphs and in FIG. 4.

The device (100) in the preferred embodiment is designed to be disposable or reusable since the nonwoven fabric of the outer layer (113) catches any pathogens. While it is reusable to a certain extent, its effectiveness gradually decreases. Pathogens caught on the outer layer (113) may also survive on the device (100) for a period of time. The length of time before disposal may depend on the recommended guidelines set by the manufacturer. However, should the device (100) in the preferred embodiment be contaminated by liquid secretions outside of droplets (e.g., blood, mucus), the device (100), including the thermal filter (114), needs to be disposed of afterward. In an exemplary embodiment, the device (100) is made of a different material (e.g., rubber or plastic) that can be reused and washed after use. This embodiment is outlined in future paragraphs describing FIG. 6.

The preferred embodiment allows for a replaceable filter piece (132) that can be placed in the clipping mechanism (130). By doing this, it can prolong the service life of the respirator (100). In another embodiment, the filter piece (132) is integrated inside the device (100). The filter piece (132) is placed in the cartridge (130) during manufacturing. As a result, the device (100) is disposed of entirely when required. This could prevent unnecessary tampering and spread of pathogens to the device (100) that may be present with a disposable or reusable N95 with a replaceable filter. Additionally, the filter piece (132) integrated during fabrication may be placed more precisely in the device (100) and inspected before distribution.

In yet another exemplary embodiment, the filter piece (132) is not used. This may reduce the effectiveness and protection since that filter piece (132) is critical in trapping the majority of airborne particles; however, the thermal filter in the chamber (112) would be adequate for killing pathogens entering the user. Additionally, the nonwoven outer layer (113) can still catch liquid droplets and some airborne particles.

The horizontal nose clip (106) is placed onto the device (100) by stitching or with an adhesive(s). This clip (106) is placed on the exterior side of the device (100), although it can also be placed inside the mask like the vertical nose clip (108). The interior vertical nose clip (108) may also be placed on the outside of the mask, though this may lead to additional and unnecessary tampering when fitting the device. Regardless of the clips' (106, 108) placement, both can be adjusted accordingly to aid in forming the chamber (112) around the person's nose and also to ensure the device (100) is better able to form a tight-fitting seal around the person's face. This will be mentioned in future paragraphs and in FIG. 3.

For a generally health-conscious person, the exhalation valve (110) allows air to circulate freely through the mask while filtering harmful material. This increases comfort to the user for prolonged periods of time, as condensation and heat do not build up rapidly. With a manual or electrically controlled exhalation valve (110), the humidity inside the chamber (112) can be maintained at a predefined level. If the valve opening is small, it will generate higher humidity inside the chamber (112) because the steam from exhalation will build up; otherwise, the humidity will be lower. In an alternative embodiment, the device (100) has no exhalation valve (110), which is in line with the exemplary face mask present in FIG. 7. The lack of an exhalation valve (110) in this embodiment is better suited for an ill person because it prevents droplets from exiting the valve (110), which may contain infectious pathogens. Therefore, the lack of this valve (110) would prevent the spread of infections and diseases to others in the surrounding area. In other embodiments, a tiny fan could be connected to the exhalation valve (110) to better expel humidity. The use of such a fan would be linked to an alternative humidity sensor that will be explained later in future paragraphs and in the description of FIG. 5.

In yet another alternative embodiment, the respirator/face mask device (100) uses filter cartridges around the exhalation valve area. This would generally ease the filter replacement of the device (100). However, the replacement of filter cartridges can be costly in the long term. Additionally, the weight of the cartridge may also weigh down the device (100), especially that of the disposable or reusable N95 respirator in the preferred embodiment. This may leave openings around the sides of the face for pathogens to enter. Therefore, the use of such cartridges would be applied with the alternative reusable respirator design outlined in the exemplary embodiment of FIG. 6.

The elastic straps (104) in the preferred embodiment are fixed in place on the sides of the respirator/mask (100) with an adhesive, stitching, or a staple. However, solely using the elasticity of the straps (104) for adjustment may limit the number of people that can use the respirator/mask (100). Furthermore, if the elastic straps (104) need to be further adjusted for fitting through unconventional means of double-wrapping, it may lead to an overall compromise to the functional integrity of the device (100). In an alternative embodiment, the sides of the respirator/mask (100) have adjustments for the straps (104) to fit around the user properly.

In other alternative embodiments of the present disclosure, the heated device (100) can be applied to other nonmedical uses, which include extreme temperature environments (i.e., cold weather), facial treatments or massage, moisture level maintenance around the face area; and so forth. Several modifications need to be made to various components of the device (100) to accommodate such uses. The benefit of using the device (100) in other applications is additional to the novel thermal filter for antiviral purposes.

Figure 2A:
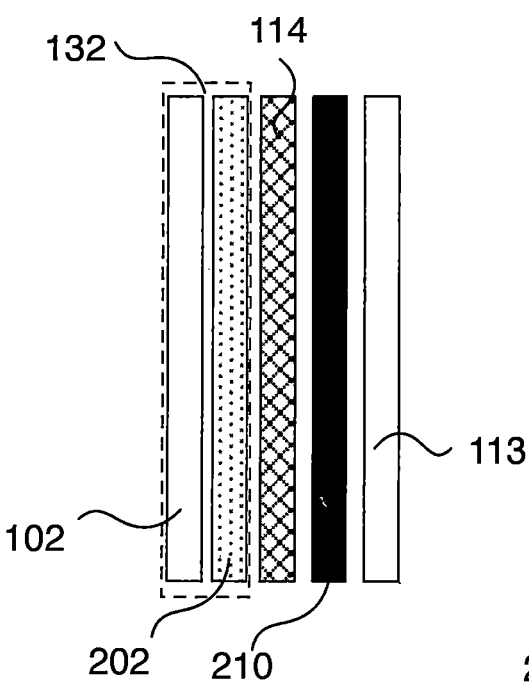
FIG. 2a illustrates the cross-section views of the filter layers of an N95 disposable or reusable respirator in an exemplary embodiment of the present disclosure.

FIG. 2 illustrates the cross-section views of the filter layers of an N95 disposable or reusable respirator in two exemplary embodiments of the present disclosure. However, it is not intended to be limited to these two specific embodiments. FIG. 2a illustrates the device layers in one embodiment where the filter layer (202) is a single layer. The outer layer (113) may be made of a nonwoven hydrophobic fabric that repels visible objects and moisture from liquid droplets lingering in the air that may contain pathogens (e.g., from someone sneezing or coughing). An optional supporting layer (210) can be implemented outside of a heating element layer (114) to provide structural integrity to the device. A filter piece (132) is placed under the heating element layer (114). Both an inner layer (102) and filter layer (202) are independent layers or part of the replaceable filter piece (132) that can be renewed periodically to prolong the service life of the device. The inner layer (102) may overlap the filter layer (202) that is made with a single nonwoven meltblown material that filters tiny particles from the air. The inner layer (102) may be a nonwoven hydrophilic fabric layer that absorbs liquid droplets from exhalation. If the inner layer (102) sometimes is also called the face cover layer, especially when it is independent of the filter layer (202).

Figure 2B:
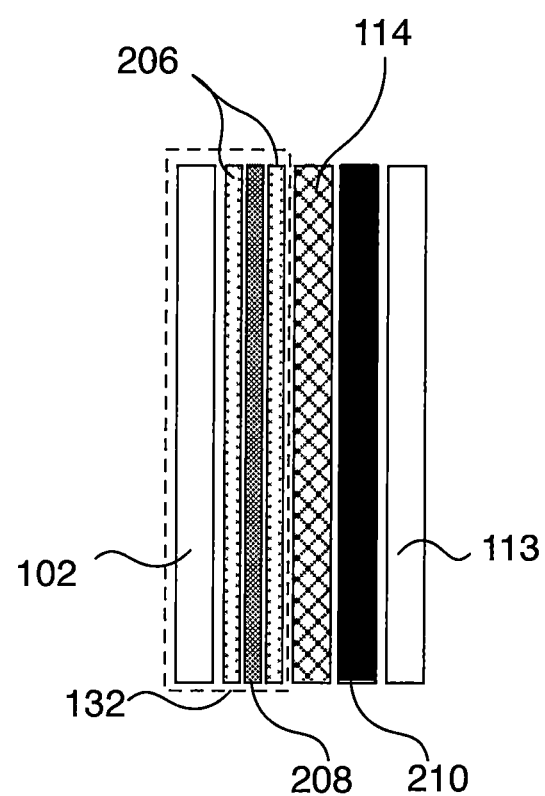
FIG. 2b illustrates the cross-section views of the filter layers of an N95 disposable or reusable respirator in an alternative embodiment of the present disclosure.

FIG. 2b illustrates an alternative embodiment with a multi-layer filter between the inner layer (102) and the heating element (114). The filter layer (202) contains two filter layers (206) for coarser particles, with a carbon layer (208) for finer particles. Additionally, the carbon layer (208) also offers protection against odors and vapors. Like with FIG. 2a, both the inner layer (102) and multi-layer filter (206, 208) make up the filter piece (132), which can be replaced periodically. The descriptions of the other three layers (114, 210, 113) from the previous FIG. 2a also apply here.

The layers outlined in this figure are considered heat-resistant. As a result, it is able to withstand high temperatures without the risk of burning. Therefore, the increased temperature of the device in the present disclosure (between 55° C. and 100° C.) would not be an issue for the layers. This temperature can be regulated with the use of a temperature controller chip; this will be further mentioned in future paragraphs and in FIG. 4.

Although the filter piece (132) is considered optional, it is considered obvious to incorporate for those skilled in the arts. The filter piece is essential when dealing with airborne pathogens without entirely blocking open spaces for breathing. This is particularly true with the embodiment shown in FIG. 2b since it can also protect against gases and odors. Furthermore, the addition of this layer is not likely to add significant weight to the device. However, the filter layer may cause breathing resistance and make it difficult for some users to use. In other embodiments of the present disclosure, there can be a filter with a lower density to allow increased air permeability. This may be done with a different grade filter found in other NIOSH-approved respirators. It should be noted that the device may not meet the NIOSH standards if the filter piece (132) is not in accordance with their standards.

The melt blowing process used for the filter (202) is a manufacturing process that converts a polymer into small micro- or nanofiber filaments, which are then integrated as a nonwoven fabric. The polymer melts and is extruded with hot, high-speed gas. The fibers are blown onto a moving substrate to form a self-bonded web. Polymers with thermoplastic properties are used, with polypropylene being one of the most common. Other materials that are used in melt blowing are polystyrene, polyurethane, polyethylene, etc. Apart from filtration, meltblown fabrics also see use as an absorbent in hygiene products, apparel products, and drug delivery. Meltblown fibers are considered ideal for filtration due to their efficiency, high porosity, and high holding capacity. Other advantages of the process itself are that it is straightforward, highly productive, and does not use any hazardous chemicals. As noted earlier, the meltblown fibers used for the filter layers (202, 206, 208) are able to withstand the high temperatures needed for the device to kill pathogens.

In an alternative embodiment, the filter piece (132) is soaked in medicinal liquid. The filter can be soaked with a variety of materials, including mint or type of Chinese medicine such as Banlangen liquid extract (a compound from Indigo Woad root). Ultimately, the type of scent is dependent on user preference. By soaking the filter piece (132), it adds an aromatic scent to the respirator/mask that is more pleasant for the user. It also allows easier respiration for the user without any compromise to the seal formed around the respirator/mask. However, it is possible that soaking the filter may compromise its function in filtering airborne matter. Therefore, it would be better to spray the medicinal liquid on the filter rather than soaking it. At the very least, a soaked filter should be completely dried before being inserted into the device.

Dealing with moisture around the mask is essential for ensuring prolonged use of the device. However, the preferred embodiment of the present disclosure is designed to be disposable or reusable. First, the filter layer's (202) effectiveness in catching pathogens decreases over time, as noted earlier in previous paragraphs. Reduced performance can be from the accumulation of moisture within the respirator, particularly the area around the exhalation valve. Additionally, the filter piece (132) can expire after two years. Therefore, a replaceable filter piece (132) means that the rest of the device can still be used without the need for an entire replacement.

Second, the hydrophilic fabric layer of the inner layer (102) ensures that the condensation from exhalation does not make contact with the user's skin. This expulsion of moisture is aided with the exhalation valve in the preferred embodiment of the present disclosure. Furthermore, the heat from the heating element (114) can be used to dry up moisture from this inner layer (102), particularly if the temperature setting is on the higher end. The hydrophilic properties of the inner layer (102) play one part in allowing the device to be worn for prolonged periods of time. However, the inner layer's (102) effectiveness in absorbing moisture gradually decreases with prolonged use, which is another reason why the preferred embodiment of the device is considered disposable or reusable with replaceable filters.

Although optional, the support layer (210) is beneficial in maintaining the integral structure of the device. This may be applied around the physical seal of an N95 respirator in the preferred embodiment, which protects against airborne particles that may contain pathogens. In another embodiment, the support layer (210) can be a cushioning layer, which may provide user comfort for prolonged use. This would be better suited in the reusable respirator embodiments since it can better support the additional weight of the cushioning.

FIG. 3 illustrates a rear, front, and side view of an N95 disposable or reusable respirator applied on a person's face in the preferred embodiment of the present disclosure. All descriptions of the device's chamber (112), nose clips (106, 108), exhalation valve (110), and heating element (114) also apply here. FIG. 3a shows the rear view of the respirator/mask's chamber (112). FIG. 3b illustrates the front view of the respirator/mask's chamber, which shows the nose (302) lining up with the nose clips (106, 108) and the mouth (304) lining up with the exhalation valve (110).

FIG. 3c illustrates two side views of the chamber with two embodiments: one without an exhalation valve (110) and another with an exhalation valve (110). Both embodiments in FIG. 3c show the exact location of the chamber (112), which forms around the user's nose (302) and mouth (304). The outer layer (113) is illustrated to meet the chin at the lower portion of the device.

The main advantage of the chamber (112) design is the thermal filter that is created around the facial areas most prone to disease transmission. Also, rather than heating the whole device, the localization of the heating concentrated around the nose and mouth area will reduce the power needed to keep the device operating, which means that it can function for a longer time. This will be mentioned again in future paragraphs.

As noted earlier, the nose clips (106, 108) must be manually adjusted accordingly to provide each user with optimal fitting and protection against pathogens. The clips (106, 108) are made of a flexible strip of metal such as aluminum, zinc, or thin gauge steel. More importantly, the adjustment of the clips (106, 108) is the key to adjusting the shape of the chamber (112) that the heat barrier will form around. The side view in FIG. 3c illustrates the vertical nose clip (108) being shaped around the person's nose (302), which curves under the tip of the nose (302). This helps further confine the thermal heat barrier to the face's external openings—the nostril of the nose (302) and mouth (304). In an alternative embodiment, there is a third clip under the mouth (304), which can be adjusted to fit the user's face and form a better chamber (112) and physical seal. The chamber (112) also makes it possible to heat the air to an extremely high temperature; for example, in case a very high temperature like 90-100° C. is needed to deactivate certain types of viruses. However, the heating element (114) may directly touch the user's skin or face. This would likely cause discomfort or burn damage.

FIG. 4 illustrates an exploded isometric view of the multiple layers of the heating element and its connection to the power switch and temperature controller chip in the preferred embodiment of the present disclosure. However, it is not intended to be limited to the specific embodiment. FIG. 4a illustrates the layers of the heating element (114). The top layer is graphene (402), which is coupled with a graphene sheet (404) with a resin material through lamination. A shielding layer (406) is located beneath the graphene sheet (404), which blocks electromagnetic radiation from the heating wire (408). The heating wire (408) coils into a zigzag shape that fits with the heating element (114). This wire (408) generates heat upon receiving electrical power. A rear cover sheet (410) is placed below these layers, which can serve as a support or integrity layer for the graphene heating element (114).

Graphene (402) is considered ideal for the heating element (114) in all major embodiments (i.e., disposable and reusable face mask, N95 respirator, and other respirators) due to its low voltage required for operation, high steady-state temperature, ultrafast response, and excellent flexibility. In addition, it is also inexpensive to produce. A time-dependent temperature profile under an applied voltage of 5V exhibits a steady-state temperature of 65° C. within five seconds. The temperature profile can also apply with higher temperatures with a different voltage and time duration. Its structural strength and low density are essential in allowing the flexibility and portability of the device in the present disclosure. The graphene's (402) molecular structure and grain orientation contribute to its superior thermal and electrical conductivity. The heating element (114) has a constant temperature distribution throughout it. Existing infrared pictures from previous studies show a uniform temperature distribution regardless of shape. This uniform heat distribution is tied to both its innate flexibility and distribution of silver particles. Graphene is also considered a zero-gap semiconductor, which contributes to its electrical conductivity and operational efficiency (i.e., its low voltage and immediate response).

The graphene sheet (404) is made of a thin metal film that has a similar thermal conductivity to graphene (402). It can serve as a support layer along with the rear cover sheet (410). For the sheet (404) to complement the graphene (402), it needs to be calibrated to allow heat transfer. Additionally, the sheet (404) needs to have a thickness of at least 50 µm. If lower than 50 µm, the heat dissipation will be weakened, and the sheet (404) may be too thin to support the heating element (114).

In an alternative embodiment, the heating element (114) may use different metals for conductivity, such as copper and steel, in place of the graphene (402). Altering the materials used for the heating element would likely affect its performance in terms of thermal conductivity and structural integrity. For example, copper can be used for its conductivity, while steel can be used for its structural strength. However, graphene (402) is generally considered superior to these two metals; its transparency and low sheet resistance help achieve the thermal and electrical conductivity required to operate. As a result, it can heat up almost instantaneously when powered on and cool down just as quickly when powered off.

The rear cover (410) in the preferred embodiment of the present disclosure uses a substrate layer made of plastic or polyester due to its flexibility, lighter weight, and cheap cost.

In an alternative embodiment, the rear cover (410) is made of ceramic, which has high structural integrity that can withstand high temperatures.

The heat generated from the heating wire (408) is eventually converted into electromagnetic waves via thermal radiation. The shielding layer (406) uses a thin metal such as nickel or copper to block such waves from reaching the graphene (402). As a result, the heating element (114) as a whole can operate without disruption. This is particularly important with the temperature regulation of the device, which is explained in future paragraphs. The shielding layer (406) also plays a role in protecting the user's face from coming in contact with electromagnetic waves that may penetrate through the skin. As a result, it reduces the chances of burns from radiation that could cause long-term damage to the user.

In yet another alternative embodiment, a temperature and/or humidity sensor can be implemented on the heating element (114) as a thin film layer. This humidity sensor could be placed around the graphene sheet (404). It could also be implemented around the shielding layer (406), which allows the sensor to interact with the heating wire (408). This would be mainly applicable in more advanced respirators, such as the exemplary reusable respirator outlined in the present disclosure. The process of how the humidity sensor works will be explained in future paragraphs and in FIG. 5.

FIG. 4b illustrates the heating element (114) connected to the USB cable (120) and power switch (122). All descriptions of the socket (116), USB cable (120), USB connectors (118, 128), power switch (122), and power switch components (124, 126) also apply here. The socket (116) has to conduct wires (412) that connect to the heating element (114). One of the conducting wires connects to the temperature and/or humidity sensor(s) (414).

The conducting wire (412) is what sends the electricity to the heating element (114). More specifically, it would send that power to the heating wire (408). In one embodiment, the conducting wire (412) can take the form of a coaxial cable with an inner conducting layer (likely made of copper) and an outer layer for insulation. Although the conducting wire (412) is short, it still exhibits a bending shape. The bending shape can save space, and the wire (412) can efficiently send electrical power to the heating element (114) with little leakage.

The power switch in the preferred embodiment has three temperature settings adjusted with the ON/OFF button (126). This temperature preference can be set to three preset settings with a power switch that switches with each click of the ON/OFF button (126). Each of these presets is indicated by an LED light (124) on the switch; with the lowest (room temperature) being blue, the middle being green, and the maximum being red. All temperature settings are capable of inhibiting pathogens with the lowest set at the minimum temperature (28° C.) for killing pathogens, the medium set at 55° C., and the maximum at a temperature of 65° C. As noted before, the temperature can reach 100° C., but it is not normally used. However, the above exemplary settings are not intended to be limited to the specific temperature numbers. In other embodiments, there can be a different number of preset temperatures ranging from one to several.

The operation of the device is programmable with a timer, which automatically shuts off the device after some time has passed. Apart from power conservation, it can also aid in the temperature regulation of the device. The device gives a warning to the user to automatically stop the heating and also indicates low battery power to the user with an orange light (124). A flashing light could be used in another embodiment, although this may consume too much power. Instead, the LED light (124) will be flashing when it is charging.

Since the power supply uses a USB (118, 120, 128) rather than a standard plug, it can be powered with any USB-power device, most prominently a laptop or a portable power bank or battery. The USB connection likely plays a role in incorporating a low voltage (5V). By incorporating a low power use through a USB connection (118, 128), the device can be powered for several hours to a whole day. However, it should be noted that the device still needs to follow the necessary electrical standards for safe usage with whichever device is connected to the respirator.

In other embodiments of the present disclosure, the device can be powered by other means. This includes a standard plug or a local electricity generator (e.g., solar power panel, windmill generator, hand crank, etc.). However, the device may not be as portable if it needs a connection to these generators. Another embodiment could use an integrated battery within the device. The battery can be changed periodically, or it can be replaceable: With the latter, local electricity generators mentioned previously can charge the battery before the device is used remotely.

In an alternative embodiment, the heating element (114) can be implemented with transistors and discrete electrical components like in some previously existing products. However, they are likely to take up more space and may be more prone to short-circuiting. It is more likely that the power switch (122) can be made of such discrete electrical components too. Likewise, the temperature sensor (414) can be integrated into the switch (122) itself. The control command can be sent to the heating element (114) via the conducting wires (412). The temperature setting of the switch (122) may send electrical signals of varying intensities or colors to indicate the preset temperature setting.

In yet another alternative embodiment, the suggested humidity sensor(s) noted earlier can work alongside the temperature sensor (414). Another conducting wire (412) would need to connect the humidity sensor(s) to the power switch or control unit (122). The temperature and/or humidity sensor(s) (414) would have trace connections on the heating element (114) to communicate with each other to determine when the heating turns on based on both temperature and humidity. Again, this would be mainly applicable in more advanced respirators, such as the exemplary reusable respirator outlined in the present disclosure. The process of how the humidity sensor works will be explained in future paragraphs and in FIG. 5.

Figure 5:
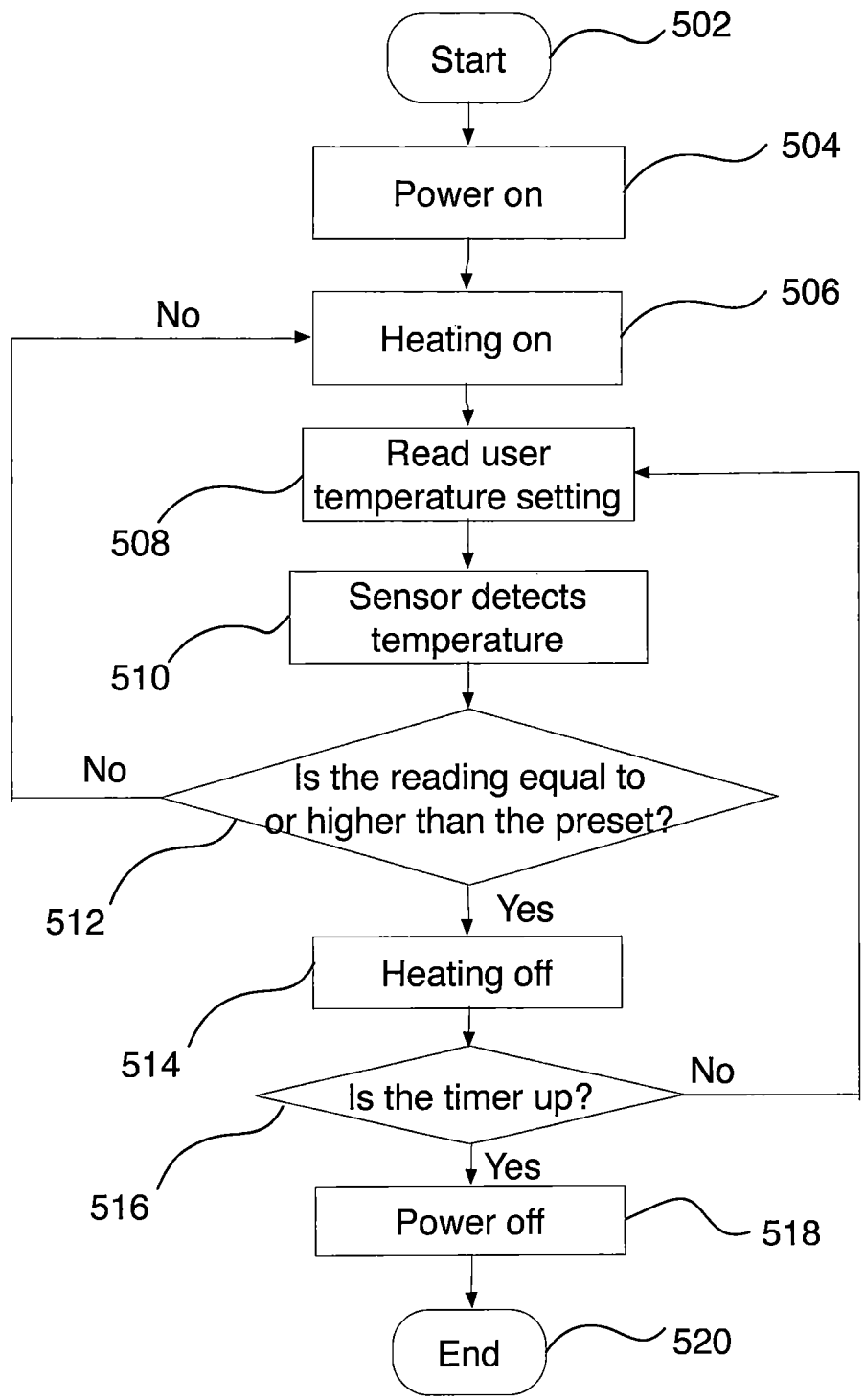
FIG. 5 illustrates a flowchart of the thermal regulation of an N95 disposable or reusable respirator in the preferred embodiment of the present disclosure.

FIG. 5 illustrates a flowchart of the thermal regulation of an N95 disposable or reusable respirator in the preferred embodiment of the present disclosure. The methods let the device operate at a consistent temperature while saving the electrical power needed to operate the device. In a non-limiting example, a built-in microprocessor executes the method and controls everything in the device, including the presets, heating, humidity adjustment, and operation timing, etc. The process starts (502) when the user turns on the device (504). Naturally, the heating or exhalation valve also turns on (506). As the temperature gradually increases, the device reads the temperature setting (508) configured on the power switch. The sensor through the temperature controller chip then detects the temperature (510) of the device.

Step (512) is where the sensor determines if the temperature reading is equal to or over the preset. If it is, the heating is turned off (514). Since the device is powered for a fixed programmable period of time, step (516) determines if the timer is up. If it is, the power will turn off (518), and the process ends (520).

If the timer is not up in step (516), then the sensor once again reads the temperature setting (508), detects the current temperature (510), and determines if the reading is equal to or over the preset (512). At this point, the device may have cooled down to a temperature below the preset, which then activates the heating (506). The sequence then continues until the user turns off the device (518), and the process ends (520).

The process applies to all major embodiments of the device: the disposable or reusable face mask, the disposable or reusable N95 respirator, and the other reusable respirator. By using this process sequence, the device is able to maintain a constant temperature and can do so without disruption during the fixed programmable timer period (516). The sensor (510) incorporated with the temperature controller chip is the key to ensure temperature regulation in the device. Furthermore, the thermal conductivity of graphene and how quickly it can heat up make the activation of this process near immediate. Without this process, the temperature may continue to increase past what it should be; this could lead to disrupted electrical function, physical damage to the mask, and reduce the service life of the device. Worse, it could cause damage to the face from burns or electrical shock.

As noted before, an alternative embodiment could incorporate a humidity sensor's function into the operational process, which works in tandem with the temperature sensor's (510) function. As noted in previous descriptions, the humidity sensor can take the form of a film layer or chip. The humidity sensor could be used to detect the humidity inside the chamber, activating the heating when the temperature falls below the preset (508, 512). In other embodiments, this sensor would work with a tiny battery-powered fan inside the exhalation valve. While it can be implemented in the preferred N95 respirator embodiment, it would be more optimal with advanced respirators that can support the weight of more powerful fans to better expel humidity.

Figures 6A, 6B:
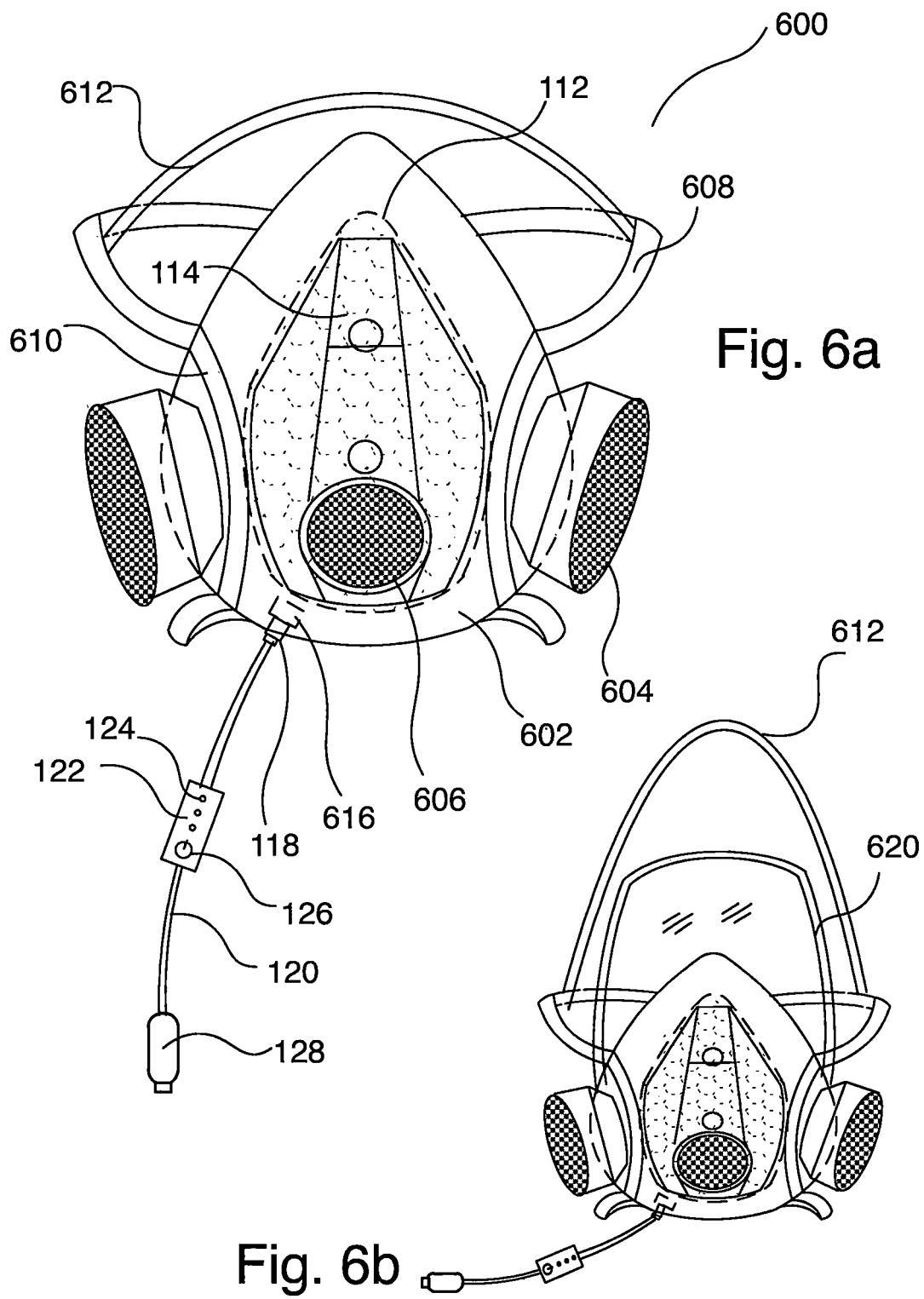
FIG. 6a illustrates an isometric view of a half-face electrically heated reusable respirator in an exemplary embodiment of the present disclosure.
FIG. 6*b* illustrates an isometric view of a full-face electrically heated reusable respirator in an exemplary embodiment of the present disclosure.

FIG. 6a illustrates an isometric view of a half-face electrically heated reusable respirator in an exemplary embodiment of the present disclosure. Like the preferred embodiment, the reusable respirator (600) contains the same chamber (112) around the nose and mouth; protected by the active thermal filter. This chamber (112) is slightly adjusted to fit the shape of the reusable respirator (600). The heating element (114) is essentially identical to that of the preferred embodiment. However, the other components are essentially different and are labeled as such. The respirator body (602) is made of a different, sturdier material such as plastic or rubber, which can be washed after each use. The reusable respirator (600) also has filter cartridges (604) on both sides of the user's face in between the exhalation valve (606). These cartridges (604) replace the filter piece (132) of the preferred embodiment but serve the same purpose. The straps of the preferred embodiment are replaced with a headband (608) divided into upper and lower segments. There is also an additional overhead headband harness (612) for extra secure placement on the user's head. Both segments of the headband (608) are attached to the reusable respirator through suspension straps (610) on both sides of the outer body (602). There is a socket (616) underneath the reusable respirator (600), which connects to the USB socket connector (118) of the power switch (122) and attached USB cable (120). All descriptions of the USB cable (120), USB connectors (118, 128), power switch (122), and power switch components (124, 126) also apply here.

One of the main features of this embodiment is the ability to switch filter cartridges (604) easily. Compared to the preferred embodiment, the filtering portion of the reusable device (600) is separate from the outer body (602). These filter cartridges (604) can be attached to the filter holder on the sides and detached when the device needs to be washed. When the filter cartridge (604) is no longer effective, it can be thrown away and replaced with new cartridges (604). In addition to ease of use, it ensures a longer service life for the device (600). Alternatively, the filter cartridges (604) have a plastic outer body that can be opened to replace the particulate filters themselves, such as the filter layers outlined in FIG. 2. In function, air flows into the cartridges, where it is filtered. The air itself travels to the user via an inhalation valve.

The filter cartridges (604) in the present disclosure are circular in shape. Other embodiments may have filter cartridges (604) with different shapes, including, but not limited to, elliptical, rectangular, etc. The filters can be cut to fit the shape of the cartridges (604). However, this shape is up to the manufacturer. Furthermore, the cartridge holders would need to be adjusted to hold the cartridge (604) shape.

The reusable respirator (600) does not incorporate nose clips that bend around the nose. Unlike the N95 respirator (preferred) and the face mask embodiments, the material used for the respirator body (600) is not flexible enough to bend. However, these clips are not necessary for the reusable device (600) since the edges are able to form a complete seal around the user's face. Furthermore, the chamber (112) is made in the shape of the protrusion at the front of the reusable respirator (600), which would be in accordance with the manufacturer's design.

Unlike the disposable medical face mask or the N95 respirator, the headband of the reusable device (600) in this embodiment is more secure due to two bands on the upper and lower sections of the device (600). Also, the overhead headband harness (612) adds an extra secure placement on the user's head. The headband (608) itself can be adjustable and made of elastic or fabric. Furthermore, the headband (608) is detachable with the use of suspension straps (610) attached to the outer body (602). The headband (608) can, therefore, be separated for separate washing or replacement if needed.

The reusable respirator (600) in the present disclosure uses a half-facepiece respirator. In another embodiment of the present disclosure FIG. 6b, a lens 620 can be considered for protecting the eyes and upper portion of the face—this type of device is known as the full facepiece respirator. While it provides better protection, the face shield may build up condensation to obstruct vision and cause discomfort. In this case, mild heating can be applied to the lens area. An incorporated humidity sensor may be able to detect humidity around the lens to activate the heating.

Figure 7A:
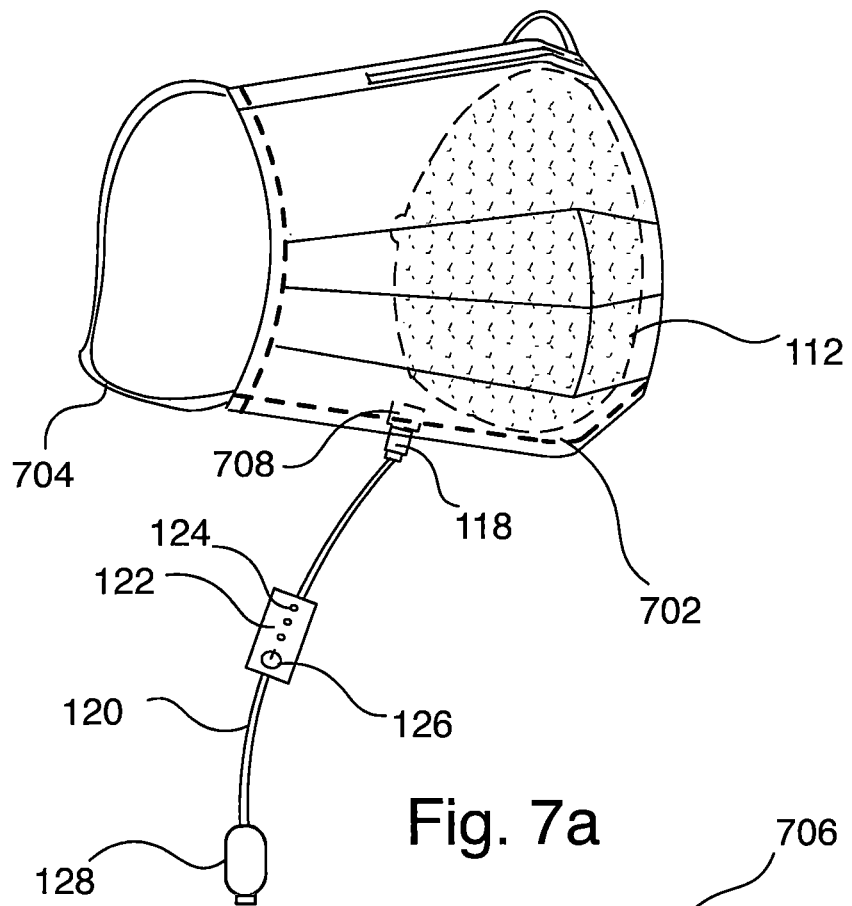
FIG. 7*a* illustrates an isometric view of the electrically heated disposable or reusable medical face mask in an exemplary embodiment of the present disclosure.
Figure 7B:
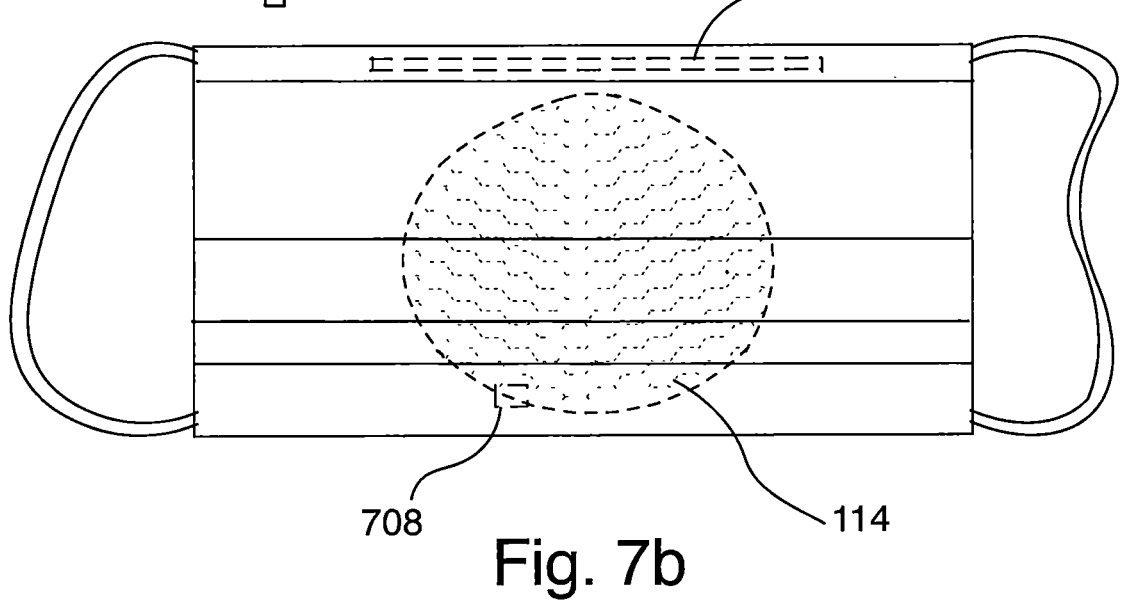
FIG. 7*b* illustrates a front view of the electrically heated disposable or reusable medical face mask in an exemplary embodiment of the present disclosure.

FIG. 7 illustrates an isometric and front view of the electrically heated disposable or reusable medical face mask in an exemplary embodiment of the present disclosure. However, it is not intended to be limited to only the specific embodiment. The same can also be applied to face masks for non-medical use. FIG. 7a shows an isometric view of the face mask, while Sub figure (b) illustrates a front view. Like the preferred embodiment, the face mask contains the same chamber (112) around the nose and mouth, protected by the active thermal filter. The heating element (114) is essentially identical to that of the preferred embodiment. In some other embodiments of the present disclosure, the heating element (114) may use a cheaper material. The outer layer of the mask (702) is made of a nonwoven fabric layer, much like the N95 respirator in the preferred embodiment. The face mask is held on the user's face with elastic ear loops (704), which are also comparable to the respirator in the preferred embodiment. There is also a nose clip (706) hidden inside the top edge of the face mask that bends around the bridge of the nose. There is a socket (708) next to the bottom portion of the element (114), which connects to the USB socket connector (118) of the power switch (122) and attached USB cable (120). All descriptions of the USB cable (120), USB connectors (118, 128), power switch (122), and power switch components (124, 126) also apply here.

All components of the disposable medical face mask are integrated, which means that the mask must be disposed of after one use. The layers of the face mask would be comparable to that of the preferred embodiment outlined in FIG. 2. Therefore, the outer layer (702) decreases its effectiveness in catching pathogens primarily from liquid droplets during prolonged use. Furthermore, there is no exhalation valve for expelling moisture and heat during exhalation. This is ideal for people who are ill because it prevents them from spreading pathogens, via coughing or sneezing, to others. In an alternative embodiment, the top of the medical face mask can be opened to allow the insertion of a filter layer. This opening would be below the nose clip (706).

With the pleated flat face mask, it is designed to fold around the user's nose and mouth. The chamber (112) is generally fixed, although the nose clip (706) can help further form the chamber around the user's face. In an alternative embodiment, a perpendicular vertical nose clip can be incorporated with the face mask embodiment. However, this may lead to extra tampering with the outer layer of the mask. Additionally, another embodiment could involve a metal clip around the bottom portion of the face mask. It should be noted that even with the extra clips, the face mask is generally not designed to have a perfect physical seal to protect against airborne particles. The seamless seal and real protection come from the heat barrier generated by the heating mechanism of the present disclosure.

In an alternative embodiment, the medical face mask can be in the shape of a duckbill. It is still loose-fitting; however, the shape can provide a slightly better physical seal. The heating element may be folded to cover both the top and bottom portions. The duckbill shape could also allow for better communication with other people, particularly between patients and health care professionals. This shape could also be applied to the N95 respirator as a separate alternative embodiment.

The invention claimed is:

1. A multiple-layer apparatus covering at least a user's nose and mouth for pathogen control, comprising:
   an outer layer;
   an inner layer close to the nose and mouth;
   an intermediate layer between the outer layer and the inner layer;
      wherein the intermediate layer comprises an electrical heating element generating a sustained high temperature enough to de-activate at least a pathogen;
      wherein the temperature is well above the human's body temperature; and
   a power source or connection providing electricity to the heating.

2. The apparatus of claim 1, further comprising a control unit that controls the electricity.

3. The apparatus of claim 1, further comprising an intermediate passive particle or droplet filter;

wherein the passive particle or droplet filter is replaceable or renewable.

4. The apparatus of claim 1, wherein the inner layer is replaceable or renewable.

5. The apparatus of claim 1, wherein the electrical heating element generates a temperature ranging from 55° C. to 100° C. to kill the pathogen; the pathogen is a virus or bacterium.

6. The apparatus of claim 1, wherein the power source is a battery and portable; the battery is rechargeable; the battery is connected via a USB interface.

7. The apparatus of claim 1, wherein the heating layer generally covers the user's nose and mouth.

8. The apparatus of claim 2, further comprising a temperature sensor; the sensor measures the temperature around the nose and mouth and provides the information to the control unit.

9. The apparatus of claim 2, further comprising a humidity sensor; the sensor measures the humidity around the nose and mouth and provides the information to the control unit.

10. The apparatus of claim 1, wherein the heating element is copper wire, graphene, or carbon film.

11. The apparatus of claim 2, wherein the power is switched on and off repeatedly at a frequency; the control unit provides multiple different frequencies for the user to choose; each frequency relates to a power level provided to the heating element and a temperature setting.

12. The apparatus of claim 8, wherein the temperature is controlled and maintained by the control unit using the temperature sensor information; if the temperature is higher than expected, the control unit switches off the heating; if lower, it switches on.

13. The apparatus of claim 9, wherein the humidity is controlled and maintained by the control unit using the humidity sensor information; if the humidity is higher than expected, the control unit switches on the heating; if lower, it switches off.

14. The apparatus of claim 5, wherein the heating layer generates the temperature within a short period of time.

15. The apparatus of claim 1, wherein the apparatus has an exhalation valve.

16. The apparatus of claim 1, wherein the apparatus is a face mask or respirator.

17. The apparatus of claim 16, wherein the respirator covers the user's entire face.

18. The apparatus of claim 16, wherein the apparatus is reusable or disposable.

19. The apparatus of claim 18, wherein the reusable apparatus is at least partially washable.

20. A method to cover at least a user's nose and mouth for pathogen control, comprising:
providing an outer layer;
providing an inner layer close to the nose and mouth;
providing an intermediate layer between the outer layer and the inner layer;
wherein the intermediate layer comprises an electrical heating element generating a sustained high temperature enough to deactivate at least a pathogen;
wherein the temperature is well above the human's body temperature;
providing a power source for electricity to the heating;
providing a control unit;
using an electrical wire to connect the heating element, power source, and control unit; and
wherein the control unit switches on and off the electricity going from the power source to the heating element.

* * * * *